United States Patent [19]

Wainwright et al.

[11] Patent Number: 5,171,537
[45] Date of Patent: Dec. 15, 1992

[54] ACTIVATED IMMUNODIAGNOSTIC PIPETTE TIPS

[75] Inventors: Norman B. Wainwright; Steven H. Boyd, both of Falmouth, Mass.

[73] Assignees: Richard E. MacDonald, Lexington, Mass.; Hugh Prior, Ocala, Fla.

[21] Appl. No.: 695,955

[22] Filed: May 6, 1991

[51] Int. Cl.⁵ ............................................. B01L 3/02
[52] U.S. Cl. ..................................... 422/100; 422/57; 435/288; 435/291
[58] Field of Search ............... 422/100, 101, 57, 58, 422/59, 99; 435/288, 292, 287, 291; 73/863.21, 863.22, 863.23, 863.32, 863.41, 863.43, 863.44, 863.55, 863.54, 863.51, 864.01

[56] References Cited

U.S. PATENT DOCUMENTS

| | | | |
|---|---|---|---|
| 2,836,979 | 4/1955 | Ryley | 73/864.01 |
| 3,985,032 | 10/1976 | Avakian | 73/864.01 |
| 4,087,248 | 5/1978 | Miles | 422/63 |
| 4,320,087 | 3/1982 | Chau et al. | 422/101 |
| 4,749,658 | 6/1988 | Jaekel et al. | 436/180 |
| 4,753,775 | 6/1988 | Ebersole et al. | 422/100 |
| 4,775,635 | 10/1988 | Ebersole et al. | 436/501 |
| 4,806,313 | 2/1989 | Ebersole et al. | 422/100 |
| 4,999,164 | 3/1991 | Puchinger et al. | 422/101 |

OTHER PUBLICATIONS

"Covalent Coupling Methods", *Methods in Enzymology*, vol. 44, pp. 138-145, 1976, Academic Press.
"New Supports in Solid Phase Sequencing", *Methods in Enzymology*, vol. 47, pp. 263-286, 1977, Academic Press.
"Target Amplification Systems in Nucleic Acid-based diagnostic Approaches", Kwoh et al., *ABL*, Oct. 1990.
"Polymerase Chain Reaction-Special Report", Arnheim et al., *Chemical and Engineering News*, Oct. 1, 1990.

*Primary Examiner*—Robert J. Warden
*Assistant Examiner*—William H. Beisner
*Attorney, Agent, or Firm*—Shlesinger, Fitzsimmons & Shlesinger

[57] ABSTRACT

The tip has intermediate its end at least two axially spaced projections which are formed on the wall of its axial bore to extend radially and part way into the bore to define therebetween a reaction chamber in the bore of the tip. A spherical receptor element is mounted in the reaction chamber for limited pulsating movement therein in response to the movement of a fluid sample into and out of the tip. Additional projections may be formed in the bore to increase the turbulence created by the sample as it moves through the tip. The spherical element is coated with a ligand having a specific affinity for a target molecule in the sample.

13 Claims, 2 Drawing Sheets

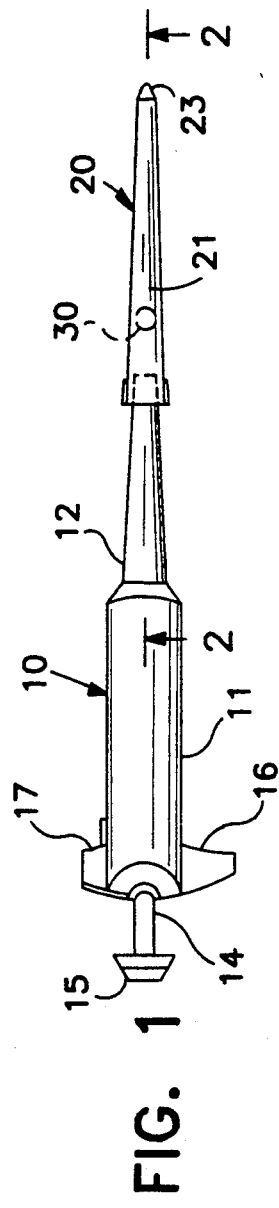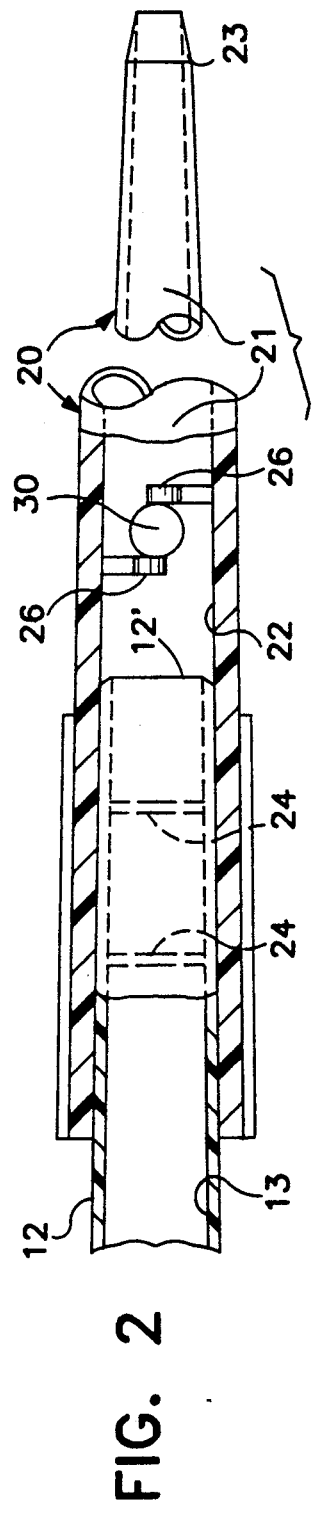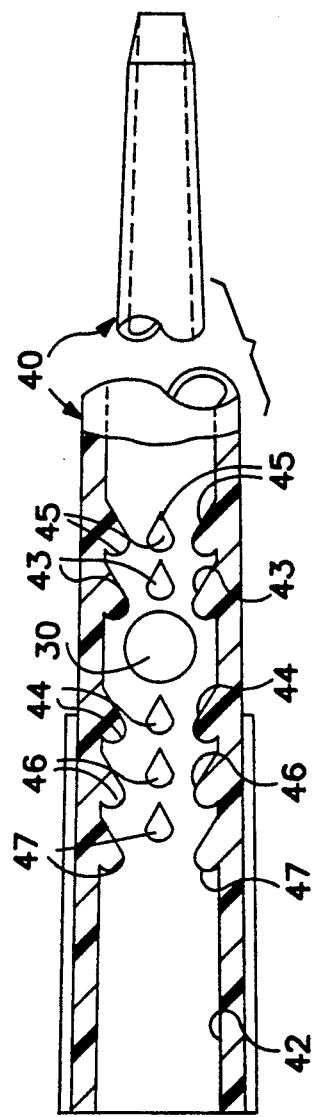

ACTIVATED IMMUNODIAGNOSTIC PIPETTE TIPS

BACKGROUND OF THE INVENTION

This invention relates to activated micropipette tips used for diagnostic test devices, and more particularly to an improved such tip which contains a reactive element which readily captures molecules from fluid samples drawn, through the tips, thus permitting such samples to be assayed more efficiently and rapidly than was heretofore possible. This invention relates also to novel methods of preparing the reactive element and assaying such fluid samples.

Existing assay formats of the type described are generally rather cumbersome and time consuming procedures, and frequently require the handling or transfer of the fluid samples and test reagents between multiple receptacles, such as for example between plastic test tubes, transfer pipettes, reaction vessels, etc. Multiple transfers of samples and/or reagents frequently result in a loss or contamination of the sample, thereby reducing the overall efficiency and sensitivity of the assay.

For example, conventional assay formats rely upon passive diffusion to bring together receptor and ligand, such as an antibody and antigen. Typically this would include the non-covalent coating of the wall or surface of a glass or plastic tube or microtiter well with an antibody, thereafter incubating a sample antigen into the coated tube or well (receptacle) to allow the antigen and antibody to bind, thereafter employing a stringent wash to remove non-specific binding, and then effecting quantitation of the bound ligand, for example by binding to a second labeled antibody.

Efforts have been made to utilize a spherical receptor bead for blood analyzing apparatus (see U.S. Pat. No. 4,749,658), but in that case the receptor was simply placed in the bore of an aspirating type cartridge, and was allowed to float freely between the operating piston of the device and the sample ingress/egress end of the cartridge. The receptor was not mounted in a disposable pipette tip designed to generate turbulence in the vicinity of the receptor upon the ingress or egress of a sample.

The related U.S. Pat. Nos. 4,753,775, 4,775,635 and 4,806,313 also disclose the use of receptors in a pipette having a bulbous upper chamber which can be flexed to cause fluid samples to be drawn or discharged past the receptors, but the receptors are not mounted in a disposable tip designed to create turbulence adjacent a receptor.

It is an object of the present invention, therefore, to provide an improved pipette tip and associated assay element which will eliminate many of the problems heretofore associated with the handling of samples during assay protocols.

To this end it is an object of this invention also to provide an improved sample transfer device in the form of a pipette tip containing a reactive element having a controlled, predetermined surface area.

Another object of this invention is to provide an improved transfer device of the type described capable of handling larger or increased sample volumes as compared to conventional microtiters or tubes.

A further object of this invention is to provide an improved transfer device containing a reaction element to which the linkage can be of the covalent or non-covalent variety.

A more specific object of this invention is to provide an improved tip of the type described which contains a novel, hydrodynamically designed receptor element for quickly capturing molecules from a fluid sample passing through such tip.

Still another object of this invention is to provide improved methods for preparing reactive elements and effecting assays of the type described.

Other objects of the invention will be apparent hereinafter from the specification and from the recital of the appended claims, particularly when read in conjunction with the accompanying drawings.

SUMMARY OF THE INVENTION

An aspirator-type pipettor is provided with a removable, hydrodynamically designed pipette tip, which has housed therein intermediate its ends a spherically shaped substrate of glass, plastic, or other polymer-based solid, the surface of which contains, or has coated thereon, any one of a number of conventional immobilization chemistries that are designed to link to proteins, nucleic acids, or other specific binding ligands by virtue of covalent attachment to reactive chemical groups, such as amino, carboxyl, sulfhydryl, etc., or by non-covalent adsorption. When a molecular sample is aspirated into the tip, it passes around the outside of the sphere, and in so doing is exposed to the chemically treated surface of the sphere which thus captures molecules that are to be assayed.

THE DRAWINGS

FIG. 1 is a side elevational view of an aspirator type pipettor or pipetting instrument having thereon a removable pipette tip of the type made according to one embodiment of this invention;

FIG. 2 is a greatly enlarged, fragmentary sectional view of this instrument taken generally along the line 2—2 in FIG. 1 looking in the direction of the arrows, but with portions shown in full;

FIG. 3 is a fragmentary sectional view generally similar to FIG. 2 but showing a modified form of pipette tip made according to another embodiment of this invention;

PREFERRED EMBODIMENTS OF THE INVENTION

Figure 4:
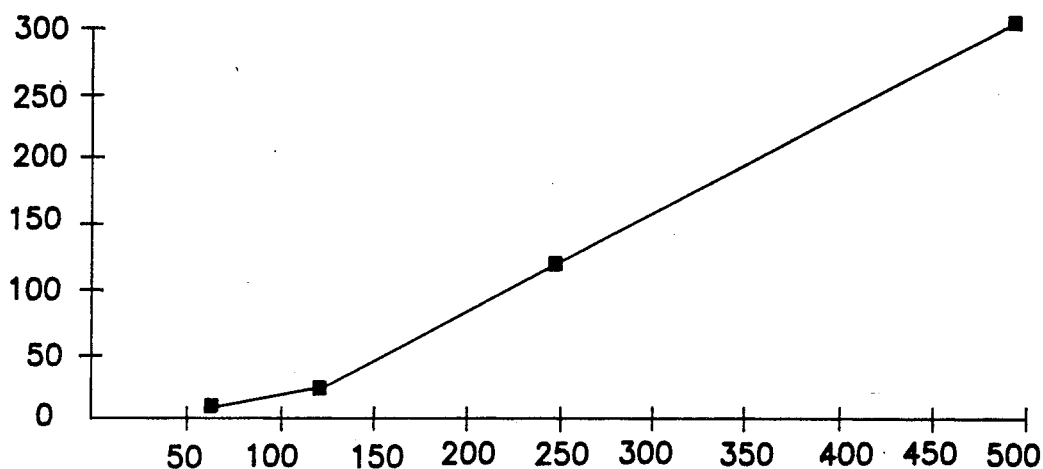
FIG. 4 is a graphical representation of the capture and quantitation of a rabbit IgG utilizing an activated pipette tip of the type shown in FIGS. 2 or 3.

Referring now to the drawings by numerals of reference, and first to FIGS. 1 and 2, 10 denotes generally an aspirator-type pipetting instrument comprising a tubular body section 11, and an integral, tapered nozzle section 12 having a bore 13 communicating with the bore in section 11. Body section 11 contains the usual plunger or piston head (not illustrated), which is attached to an operating rod or shaft 14 that projects slidably out of the end of section 11 remote from nozzle section 12. Attached to the outer end of rod 14 is the usual operating head 15, which can be used manually to manipulate the aspirator plunger in known manner. Conventional finger grips 16 and 17 also project from section 11 for use in holding and manipulating the instrument.

Removably secured over the open end of nozzle section 12 is a novel pipette tip which is denoted generally by the numeral 20. Tip 20 comprises an elongate tube of plastic, or the like, which is generally conical in configuration, including both its external surface 21, and its internal, axially extending bore 22. Remote from its smaller end 23, the tip 20 has formed on its inner peripheral surface a pair of circumferential, axially spaced projections or ribs 24, which frictionally and removably engage the outer peripheral surface of the nozzle section 12 sealingly to connect the bore 22 in tip 20 through the nozzle section 12 with the bore in the aspirator section 11. With the tip 20 mounted in this manner, the open end or nose 12' of the nozzle 12 projects only part way into the larger end of the tip 20 remote from its smaller end 23.

Also integral with and projecting radially inwardly from the inner peripheral surface of the tip 20, and part way into its bore 22, is a plurality of axially and angularly spaced ribs or tabs 26, only two of which are shown in FIG. 2. The tabs 26 project radially inwardly from the inner peripheral surface of tip 20 for substantially greater distances than do the ribs 24, and are axially spaced from the ribs 24 sufficiently so that when the tip 20 is mounted on the nozzle section 12 the tabs 26 are axially spaced inwardly of the tip from the nose 12' of nozzle 12.

Mounted in the bore 22 in tip 20, and lodged between its axially spaced tabs 26, is a spherically shaped element 30, which is coated or impregnated with a reactive receptor substance of the type described in greater detail hereinafter. The purpose of this construction is that, when a fluid sample is aspirated into the instrument 10, it will be caused to pass around the outside of element 30 as it passes through the bore 22 in tip 20 toward the nozzle section 12. The fluid dynamics created as the sample fluid passes around element 30, which simply by way of example may have a diameter in the range of 3-4 mm., will cause the sample to interact with the reactive surface of the element, thus enhancing molecular association many fold over that which would be effected by utilizing the more conventional, static diffusion format such as described above. Moreover, as noted hereinafter, subsequent receptor-ligand binding, washing (eluting) and quantitation are likewise accelerated by virtue of aspirating the sample into this type of instrument.

In FIG. 3, the numeral 40 denotes a modified tip which is generally similar to tip 20, except that the element 30 is lodged in the bore 42 of the tip 40 between two axially spaced sets or arrays of projections 43 and 44, respectively. The projections 43 and 44 of each set thereof (there being four in each set in the embodiment illustrated) are integral with and project radially inwardly from the inner peripheral surface of tip 40 at equiangularly points around its longitudinal axis. Each of the projections 43 and 44 is generally tear-drop shaped in configuration, and have their pointed ends facing the smaller end of the tip. Projections 43 are disposed between element 30 and the smaller end of tip 40, while the projections 44, which in the illustrated embodiment are larger than projections 43, are interposed between element 30 and the larger end of tip 40. Element 30 is positioned in the tip by inserting it through the larger end of bore 42 and forcing it axially beyond projections 44, which flex slightly, and into the reaction chamber defined by the space in bore 42 between the two sets of projections 43 and 44.

To enhance the turbulence created when fluid samples are drawn into or discharged out of bore 42, additional arrays of tear-shaped projections may be formed in the bore 42, such as for example the projections 45 (FIG. 3) between projections 43 and the smaller end of tip 40, and the two additional arrays of projections 46 and 47 interposed between projections 44 and the larger end of the tip. Also, while successive arrays of tips 43-47 are illustrated as being in axial alignment or registry, adjacent arrays thereof preferably are angularly offset from each other about the tip axis.

It is to be noted that the internal diameter of that portion of each tip 20 and 40, which surrounds element 30, as well as the axial space separating its respective projections 26 and 43, 44, is greater than the diameter of the element 30 so that the element is free to move or rotate in the reaction chamber defined between the respective projections 26 or 43, 44 as a sample is aspirated into the associated instrument, thus enhancing the interaction between the sample and reactive surface of element 30.

A number of examples of sample test procedures using tips of the type disclosed above are as follows:

EXAMPLE 1

Immobilization of Protein A, Capture and Quantitation of IgG

An activated pipette tip—i.e., one containing a receptor in the form of a coated element 30, was prepared by coating a glass sphere (3 mm diam.) with amino silane and reacted with glutaraldehyde according to standard procedures. (See for example, *Methods in Enzymology*, Vol. 44 of 1976, pp. 138-145, and Vol. 47 of 1977, pp. 263-286, Academic Press, N.Y.N.Y.). The coated sphere 30 was inserted into a polypropylene micropipette tip of the type denoted for example at 40 in FIG. 3. The sphere became lodged in the reaction chamber as defined by the space between the projections 43,44, which are designed to maximize turbulence of the aspirated sample as it flows around the sphere.

(a) Protein Immobilization

The conditions for covalent protein immobilization are dependent on factors such as concentration, time, and to a lesser extent pH, ionic strength and temperature. In this example protein A was immobilized to the coated sphere at a concentration of 0.5-2.0 mg/ml by the following steps:

1. Coupling:

Potassium phosphate buffer (0.05M, pH 8.5) was employed, and is recommended, although coupling can be performed between pH 7-10. Coupling at room temperature is recommended. For lower temperatures, e.g. 4° C., a longer immobilization time is required. A 0.05-1 ml. solution of Protein A was exposed to the coated sphere by slowing pipetting the solution in and out of the tip (1-5 minutes). This can be done also by holding the solution in the pipette tip and statically incubating the solution (1-5 minutes).

2. Capping (Blocking):

For this step Monoethanolamine 10% (v/v) in 0.5M sodium bicarbonate, pH 9.5 was used. Other blocking solutions that function well are 1M glycine, 10% bovine fetal serum and 2% milk or Blotto (Bethesda Research Labs) 0.5 0 1.0 ml.

3. Wash 1:

1.0M NaCl, 0.1M TRIS buffer, pH 7 was used to remove all non-covalently bound protein from the tip. A wash solution in the amount of 0.05–1.0 ml was pipetted through the tip, and repeated three times.

4. Wash 2:

1 ml of distilled water or PBS was passed through the tip and repeated three times.

(b) Assay Procedure

Phosphate and TRIS buffered saline (PBS or TBS) containing Bovine Serum Albumin (2% w/v)/Tween-20 (0.1%, v/v) were used as the assay dilutents. The wash solutions were PBS or TBS/Tween-20 (0.1% v/v).

Since Protein A binds specifically to a number of immunoglobulins of the IgG type, the immobilized Protein A in the tip can capture IgG from a solution allowing detection in less than 10 minutes. Antibody capture was employed in a number of immunological diagnostic assays. Rabbit IgG, coupled to horseradish peroxidase (HRP), was serially diluted in a standard multi-well microtiter plate and detected in the following protocol. Solutions were passed through the tips using standard micropipette aspirators or like devices.

Protein A Protocol

Step 1. Washed 3 ml of PBS through the tip to remove the shipping buffer.

Step 2. Exposed the coated sphere in the tip to Rabbit IgG for 5 minutes, and then washed with 3 ml. of PBS.

Step 3. Quenched excess Protein A with non-rabbit IgG, for 5 minutes, and then washed with 3ml. of capping solution and 3 ml of PBS. Step 4. Exposed the coated sphere to enzyme linked anti-antibody (1/500–1/5000) for 5 minutes and washed with 3 ml. of PBS. Step 5. Added soluble enzyme substrate (200 ul) and incubated for color development. Read at 690 nm. in a spectrophotometer.

The results are represented graphically, as shown by reference to FIG. 4.

EXAMPLE 2

The novel tip and its coated sphere 30 was employed also in a standard "Sandwich" immunoassay. In such case accelerated ELISA formats were accomplished using primary antibodies, Protein A/G or any protein/peptide with a demonstrable affinity for a specific target molecule. For this example, labelled antibody detection protocol included:

Step 1. Washed tip with PBS (3 ml) was followed by exposure of the coated sphere 30 to an Antibody (Rabbit labeled HRP) for 5–10 minutes.

Step 2. Washed with PBS (3 ml) and capped with a capping agent for five minutes.

Step 3. Washed with PBS (3 ml) and added soluble substrate for HRP.

Step 4. Read OD at 690 nm in multiplate spectrophotometer.

EXAMPLE 3

Miniature High Efficiency Affinity Separations

One may take advantage of the enhanced flow dynamics of the novel tip disclosed herein to achieve rapid, highly efficient separations based on standard ion exchange, reversed phase, hydrophobic interaction, immunoaffinity, or other affinity ligands popularly employed in column chromatography. Since the solution containing the molecule to be purified passes over a single sphere, and interacts efficiently with the surface only, very rapid purification of protocols is achieved.

In this example, a glass sphere is coated with octydecyl silane (C-18). This C-18 ligand is used to bind proteins from a dilute solution for further analysis. 5 ml of human urine is exposed to the C-18 coated sphere 30 in the tip 20 or 40 by multiple pipetting (fluid is drawn up and down around the sphere ten times). The tip is washed with 1 ml. PBS three times. Protein is eluted from the tip by multiple pipetting 0.1 ml. of 25% ethanol. Proteins in the urine such as Human Chrionic Gonadotropin are eluted into the 0.1 ml of 25% ethanol and thereby concentrated 100 fold for further analysis by immunological assay or gel electrophoresis.

EXAMPLE 4

Use in a Polymerase Chain Reaction

Polymerase Chain Reaction (PCR) has become a routine tool for amplifying segments of DNA or RNA. *(Polymerase Chain Reaction,* Norman Arnheim and Corey H. Levenson, C&EN, Oct. 1, 1990 pp. 36–47, and *Target Amplification Systems In Nucleic Acid-Based Diagnostic Approaches,* Deborah Y. Kwoh and T. Jesse Kwoh, ABL, October 1990, pp. 14–25). The protocol includes incubation of the target nucleic acid with specific primers flanking the region to be amplified. DNA polymerase is allowed to extend the annealed primers in multiple rounds of primer extension, duplex melting and primer extension. One of the problems encountered in this technique is that for most efficient cloning or further analysis of the amplified nucleic acid, excess primer must be removed. This typically involves a cumbersome column chromatography step. By incorporating onto the sphere 30 in the tip 20 or 40, a DNA binding ligand, such as chitin, DNA binding protein, hydroxylapatite, etc., an affinity elution can quickly separate the amplified nucleic acid from excess primer and enzyme. The reaction mix is allowed to contact the coated sphere for 1–5 minutes. After three 1 ml. washes, the amplified nucleic acid is removed by exposure to the eluting buffer.

Alternatively, the primers may be covalently immobilized onto the coated sphere 30. This may be accomplished via a linker arm comprised of a DNA sequence utilized as a restriction enzyme site. The polymerase chain reaction may proceed in the reaction chamber of the tip—i.e., the chamber containing sphere 30. At the completion, the amplified DNA may be removed from the tip by the addition of the restriction enzyme whose recognition sequence is on the linker. The amplified DNA may then be separated from residual enzyme by organic extraction.

EXAMPLE 5

Restriction Enzyme Extraction

The activated tip 20 or 40 can be used as an alternative to organic (phenol/chloroform) extraction to remove enzymes from small volume reactions, such as the polymerase in the PCR technique or restriction enzymes after restriction enzyme digestion of DNA. After restriction enzyme digestion, it may be necessary to remove enzymes prior to cloning. Not only are phenol and chloroform highly toxic, but they must frequently be obtained in very pure form to eliminate contaminants that adversely affect nucleic acids. The tip 20 or 40 with a sphere 30 preactivated to covalently capture proteins by reacting with available amino groups can effectively bind enzyme and leave purified DNA in solution by the following procedure:

1—Incubate 1 ug pBR322 DNA with 3 units of EcoR1 enzyme at 37° C. at a volume of 100 ul for 1 hour.
2—Expose the entire reaction mixture to the coated sphere in the tip by multiple pipetting for 1 minute.
3—The remaining reaction solution is free of enzyme and can be used directly for cloning procedures.

It is to be understood also that the above-noted novel pipette tip and its associated receptor element 30 can be utilized for capturing whole cells or micro-particles for subsequent detection. For example, whole cells may be used for certain diagnostic procedures, including chromosome characterization; extraction of cellular nucleic acid (DNA/RNA) for hybridization analysis, sequencing, or PCR amplification; immunological characterization; or characterization by subsequent growth in selective media. The population of cells desired may be in very dilute suspension, such as bacteria in a water sample, or as a minor population of cells in a complex mixture of cells, such as a specific cell type in blood. Actuate and sensitive detection of cellular signals (i.e., DNA, RNA, proteins) will depend on accumulating and therefore concentrating the particular cell type desired, especially when a critical mass of cells is necessary to reach a minumum threshold for a particular assay. Accordingly, this sphere 30, as used in either the tip 20 or 40, could be coated with a capture ligand to effect capture and concentration. In such case the capture ligand could be as general as a positively or negatively charged surface, as in an anion or cation exchanger, or as specific as an antibody reactive with a cell surface antigen.

EXAMPLE 6

Capture Of Whole Bacterial Cells

Whole bacterial cells were captured from a dilute suspension of pond water for subsequent analysis by immunological reactivity. The method involved:

1. A tip was prepared containing a glass sphere 30 coated with rabbit IgG reactive to *E. coli* strain 0-128 surface antigens.
2. *E. coli* 0-128 at 1,000 to 100,000 cells/ml. were passed through the tip ten times.
3. The captured cells were washed in PBS with 0.05% Tween (PBST) and exposed to a mouse monoclonal antibody to a second surface antigen on strain 0-128.
4. This sphere 30 was again washed three times with PBST.
5. The sphere 30 was then exposed to Goat anti mouse IgG coupled to the enzyme Horseradish Peroxidase.
6. This sphere 30 was again washed three times with PBST, and was thereafter exposed to chromogenic HRP substrate to develop color.

For many years silica has been used for collecting, by general adsorption, such molecules as alkanes, unsaturated hydrocarbons, sugars, proteins, etc. Typically the attachment of the molecules to raw silica has been achieved through rather weak, non-specific interaction with its surface. However, it has been discovered that by the addition of certain chemical groups, it is possible to create a so-called functionalized bead to which antibodies or protein A can be covalently linked to a coated silica bead surface. For example, one such surface can be functionalized with amino or carboxyl groups by silanization—i.e., trichloro or trimethoxy silanes.

EXAMPLE 7

Fixation of Proteins Having a COOH Group by Carbodiimide Method

1. Wash 25 gr. of amino trimethoxy silanized silica beads with 0.5 m. NaCl with a pH adjusted to 4-5 wash buffer.
2. Weigh out 2 gr. of the desired protein, for example bovine serum albumin (BSA), lysozyme, ovalbumin, etc., and dissolve completely in 0.5 m. NaCl with pH 4-5 buffer.
3. Mix the aqueous protein solution with the above-noted beads.
4. Add 60 mg. of EDE (N-ety-N'-3-dimethyl aminopropyl) carbodiimide hydrochloride to the bead and protein solution.
5. Gently swirl the mixture with a slow plate mixer for 4 hours with no bead motion at room temperature.
6. Wash with three liters of 1 m. NaCl and insert into IDT.

From the foregoing, it will be apparent that the present invention provides relatively simple and inexpensive means for significantly reducing the time and costs heretofore required for effecting immunoassay of fluid samples. By using a coated spherical element positioned in the path of samples aspirated or otherwise drawn through a micropipette tip of the type disclosed herein, the resultant fluid dynamics cause a somewhat pulsating and rolling movement to element 30, and thus considerably enhance the molecular association between the sample and the coated receptor surface of the element, of course, this method thus expeding also the overall assay procedure.

Figure 5:
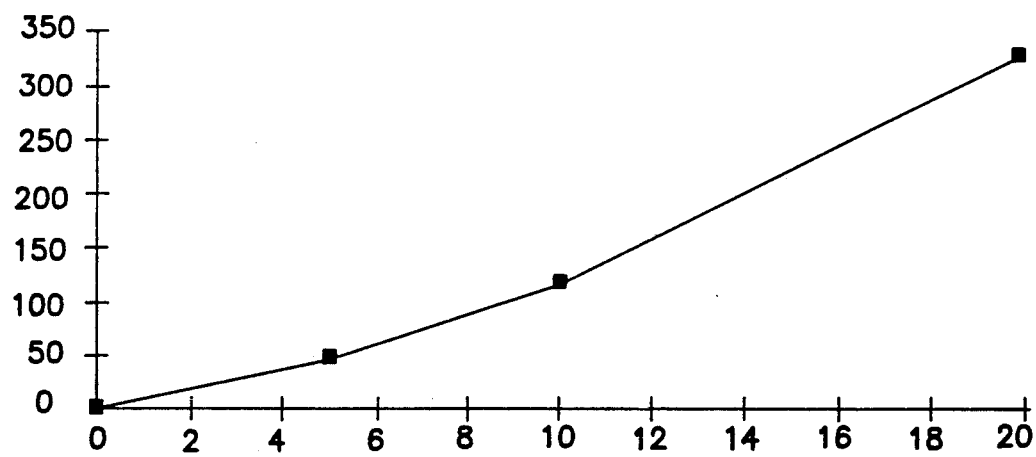
FIG. 5 is a graph showing the rate of capture of the IgG.

Note for example FIG. 5, which displays graphically the results of a time experiment with coated receptor spheres 30, and which demonstrates the rate of binding of proteins to a sphere. In this experiment constant amounts of Horseradish Peroxidase (HRP), labeled rabbit IgG at 1 ul/ml in 200 ul aliquots, were exposed to tips containing the receptor spheres 30 for different times—namely 5, 10 and 20 minutes. This study indicates the rate of which bonding occurs when using the receptor spheres 30 contrasts remarkably with experiments using microtiter plate binding protocols, which usually require 2 to 4 hours to achieve similar results.

While this invention has been illustrated and described in detail in connection with only certain embodiments thereof, it will be apparent that this application is intended to cover any such modifications as may fall within the scope of one skilled in the art or the appended claims.

We claim:
1. A disposable pipette tip, comprising
   a tubular member having therethrough an axial bore one end of which is insertable over the nozzle of a pipettor releasably to connect said member to said pipettor,
   a plurality of projections formed on the wall of said bore in said member and projecting radially inwardly of said bore,
   at least certain of said projections being axially spaced from each other in said bore and defining in said bore intermediate the ends thereof a reaction chamber through which fluid passes upon operation of said pipettor, and a coated receptor element mounted for movement with in said reaction chamber in the path of the fluids passing through said chamber, said receptor element being smaller in size than said chamber, whereby fluid flows around the outside of said element upon passing through said chamber, and said certain projections being operative to impart turbulence to the fluid passing through said chamber, whereby said turbulence in turn imparts pulsating movement to said receptor element in said chamber.

2. A disposable pipette tip as defined in claim 1, wherein said certain projections include, a first projection interposed between said element and said one end of said bore, and a second projection interposed between said element and said opposite end of said bore.

3. A disposable pipette tip as defined in claim 2, wherein said first projection is one of a first plurality of angularly spaced projections arranged in a circular array around said bore wall between said element and said one end of said bore, and said second projection is one of a second plurality of angularly spaced projections arranged in a circular array around said bore wall between said element and said opposite end of said bore.

4. A disposable pipette tip as defined in claim 3, wherein the projections in said first plurality thereof are angularly offset about the longitudinal axis of said bore relative to the projections in said second plurality thereof, whereby said first plurality of projections register axially with the spaces between said second plurality of projections.

5. A disposable pipette tip as defined in claim 4, wherein said projections are generally tear-drop shaped in configuration and have pointed ends facing in the axial direction of said bore.

6. A disposable pipette tip as defined in claim 4, wherein said projections in one of said first and second pluralities thereof are larger than, and project radially further into said bore, than the projections of the other plurality thereof.

7. A disposable pipette tip as defined in claim 1, wherein said element is coated with a receptor comprising a single ligand having an affinity for a specific target molecule in the fluid that is to be drawn into and discharged from said chamber.

8. A disposable pipette tip as defined in claim 7, wherein said coated element is a silanized bead, and said target molecule is selected from the group consisting of a protein, a carbohydrate and a nucleic acid.

9. A disposable pipette tip as defined in claim 8, wherein said bead has thereon an octydecyl silane coating.

10. A disposable pipette tip as defined in claim 7, wherein said receptor element is a polymer-based sphere coated with amino silane reacted with glutaraldehyde.

11. A disposable pipette tip as defined in claim 7, wherein said ligand is a DNA binding ligand.

12. A disposable pipette tip as defined in claim 1, wherein said receptor element has a curved outer surface.

13. A disposable pipette tip as defined in claim 12, wherein said receptor element is spherical in configuration.

* * * * *